US00PP10069P

Jnited States Patent [19]

ent

[11] Patent Number: Plant 10,069

[45] Date of Patent: Oct. 14, 1997

[4] BROMELIAD PLANT NAMED 'GUZ 210'

[5] Inventor: Jeffrey C. Kent, San Diego, Calif.

[3] Assignee: Kent's Bromeliad Nursery, Inc., Vista, Calif.

[1] Appl. No.: 563,011

[2] Filed: Nov. 27, 1995

[1] Int. Cl.[6] ..... A01H 5/00

[2] U.S. Cl. ..... Plt./88.8

[58] Field of Search ..... Plt./88.8

*Primary Examiner*—Howard J. Locker

*Attorney, Agent, or Firm*—Frank B. Robb; John H. Vynalek

[57] ABSTRACT

A sport of Guzmania 'Minnie-Exodus' (unpatented) which differs from other Guzmania in the fact that it has tri-colored variegated leaves, white tipped floral bractlets and deep red inflorescence.

1 Drawing Sheet

This present invention relates to Bromeliads and, prima-, to a Bromeliad which is the product of division of a ort of the parent Guzmania 'Minnie-Exodus' (unpatented) ich is a hybrid of *Guzmania zahnii*×*Guzmania lingulata* inor'. The plant of this invention was a naturally occur-g, vegetative sport discovered as a single plant growing in lanting of 'Minnie-Exodus'.

In point of fact, the plant is the product of a long period development which I have conducted over many years in effort to provide plants of the Bromeliad family which commercially desirable and healthy as far as being able ship and display.

As a result of this program, I have developed the instant iety and selected the same from a sport of Guzmania as licated herein and this particular plant, I denominate 'Guz )'.

I have caused the plant to be reproduced by division in the ghborhood of Rancho Santa Fe, Calif. and found that er time as a result of such asexual reproduction and ntinuing reproduction the plant holds true from generation generation.

Generally speaking, this sport is distinguished from other nts resulting from other Guzmania by expressing a dif-ent color combination and is colorful even when not in wer. The plant of this invention is identical to the 'Minnie-odus' except for the tri-colored variegation of the leaves, white tipped flower bractlets and the deep red inflores-ice. Due to the tri-colored effect of the leaves, it is similar effect to 'Guz 214' except this plant has more leaves, oximately 6 to 10, more color on the leaves, is more red n 'Guz 214' and the inflorescence is differently shaped. e white tips on the floral bractlets are an added attraction, color in the inflorescence lasts eight to ten weeks.

BRIEF DESCRIPTION OF THE DRAWING

I append hereto a color illustration of a typical plant of my v variety and is shown as near the actual colors of the nt as photo reproduction of this kind can depict.

Color values presented in this disclosure were taken from Munsell Color Cascade. Color definitions of ordinary aning are presented where appropriate and properly scriptive. Colors are approximate as color depends on ticultural practices such as light level and fertilization e, among others, without, however any variance in geno-e.

In order to point out more specifically the most notable ects and novel characteristics of the plant of this invention, as set forth above, the following detailed botanical description presents the general as well as the specific characteristics of 'Guz 210'.

General characteristics:

*Type.*—Monocot, perennial.

*Habit.*—Medium, vigorous, upright, spreading and dense.

*Hardiness.*—Tender.

*Size.*—About 25 to 27 inches in width and about 18 to 20 inches, including inflorescence, in height.

*Shape.*—Vase formed.

Leaves:

*Length.*—20 to 22 inches.

*Width.*—1¼ inches. Medium size, acuminate, acutely pointed, medium thickness, light green and smooth.

*Color.*—22-11 on obverse and 22-14 on reverse; Variegated longitudinally with 25-1 color; Variegation varies in width and is flushed with 45-6 on obverse and stained with 43-8 on reverse, more heavily at base of leaves.

*Margin.*—Smooth.

Inflorescence: Branched.

Flower buds: Tender, medium, conic and appressed.

Bracts:

*Primary bracts.*—Linear acute with same variegation as the leaves; Size of bracts about 7 inches×1 inch; Color 25-1.

*Floral bract.*—Acute; Size about 5 inches×1 inch decreasing in size to about 3 inches×1 inch at apex; Color 41-13 (obverse and reverse), unvariegated.

*Flower bractlets.*—Clasping the flower; Color 41-13, tipped 25-1.

Flowers: Cylindrical corolla; Color 25-1 at anthesis; Petals half open at anthesis.

Reproductive organs: Six stamen, two joined to each petal ¼ of the distance from the base, stigmata while, sterile $F^1$ hybrid, infertile.

It is claimed:

1. A new and distinctive cultivar of Guzmania plant named 'Guz 210', as described and illustrated, characterized particularly as to novelty by the tri-colored variegation of its leaves, white tipped flower bractlets and deep red inflorescence.

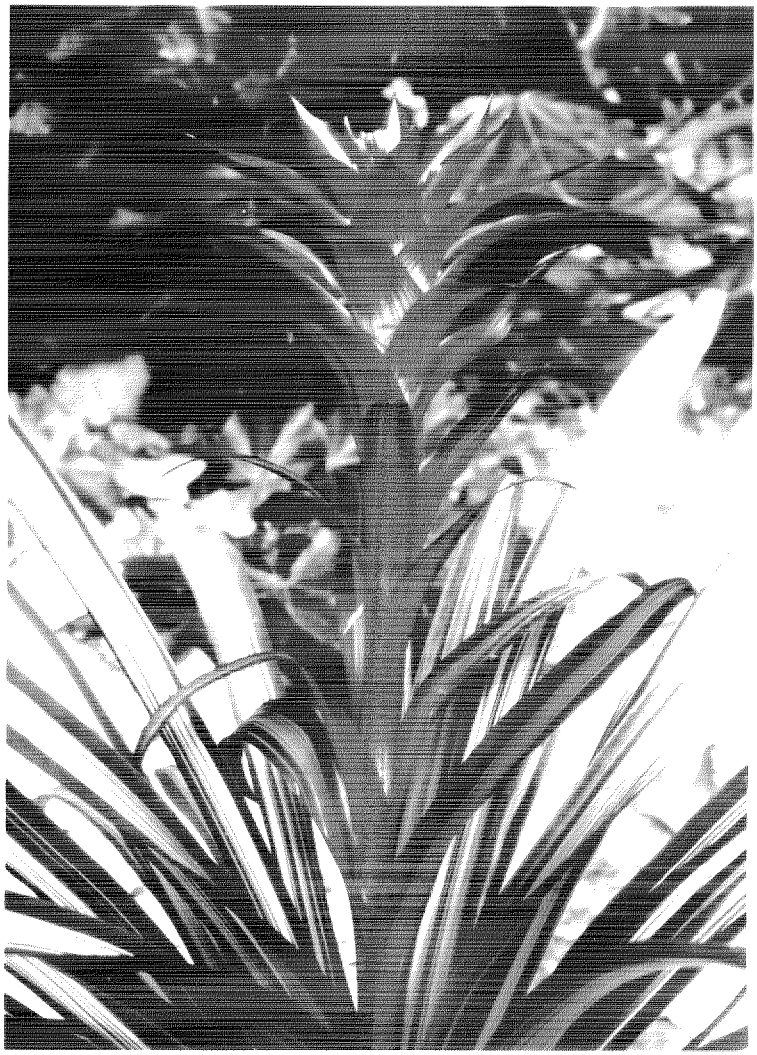

* * * * *